United States Patent [19]

Mennen

[11] 4,018,653

[45] * Apr. 19, 1977

[54] **INSTRUMENT FOR THE DETECTION OF *NEISSERIA GONORRHOEAE* WITHOUT CULTURE**

[75] Inventor: Frederick C. Mennen, La Porte, Ind.

[73] Assignee: U.S. Packaging Corporation, La Porte, Ind.

[ * ] Notice: The portion of the term of this patent subsequent to Apr. 8, 1992, has been disclaimed.

[22] Filed: Dec. 30, 1974

[21] Appl. No.: 537,593

Related U.S. Application Data

[62] Division of Ser. No. 193,739, Oct. 29, 1971, Pat. No. 3,876,503.

[52] U.S. Cl. .............................................. 195/127
[51] Int. Cl.$^2$ ......................................... C12K 1/10
[58] Field of Search ............ 195/103.5 R, 127, 139

[56] References Cited

UNITED STATES PATENTS

| | | | |
|---|---|---|---|
| 2,970,945 | 2/1961 | Free et al. .................. | 195/103.5 R |
| 3,446,596 | 5/1969 | Salivar et al. .................. | 23/253 TP |
| 3,450,129 | 6/1969 | Avery et al. ........................ | 195/139 |

OTHER PUBLICATIONS

Hartman, Miniaturized Microbiological Methods, Academic Press, New York, p. 5 (1968).

Primary Examiner—Alvin E. Tanenholtz

[57] ABSTRACT

A non-culture method and instrument for a rapid presumptive test for gonorrhea in which a specimen of exudate from a suspected case is placed in direct contact with a pledget containing a compound which reacts with *Neisseria gonorrhoeae* to produce a color change. The pledget, before the test, is in a dry condition and is activated by a wetting agent such as saline, when placed in contact with the pledget. The chemical compound used and incorporated into the pledget is selected from a group consisting of phenylenediamines. The instrument used consists of a flexible tube containing a fluid-filled frangible ampul at one end and the chemically impregnated pledget disposed immediately above same. A separate sterile swab is supplied for taking the specimen. The swab containing the specimen is inserted into the flexible tube. The flexible tube is then squeezed at the ampul portion, releasing the wetting agent by breaking the frangible ampul. The wetting agent when thus released activates the reagents in the pledget. A downward pressure of the swab containing the specimen places it in direct contact with the activated pledget. If gonorrhea is present in the specimen on the swab, a distinctive coloration of the specimen takes place within two minutes.

4 Claims, 2 Drawing Figures

U.S. Patent  April 19, 1977  4,018,653
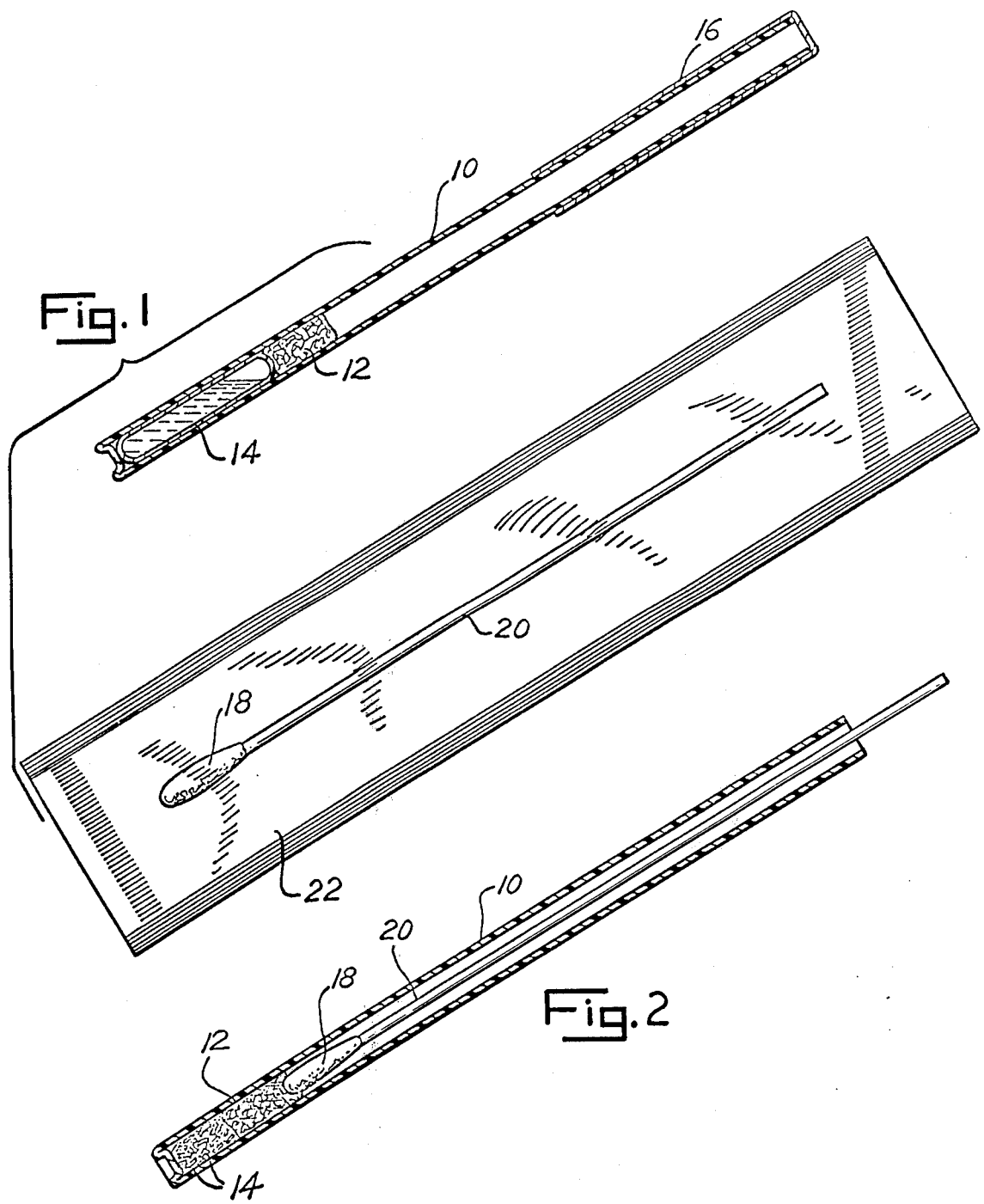

INSTRUMENT FOR THE DETECTION OF *NEISSERIA GONORRHOEAE* WITHOUT CULTURE

This is a division of application Ser. No. 193,739, filed Oct. 29, 1971, now U.S. Pat. No. 3,876,503.

It is common knowledge that this country and most of the world is undergoing a venereal disease epidemic. In the United States alone the disease has reached pandemic proportions. It is estimated that only one-fifth of the cases are reported and only one-third reach the attention of physicians and Public Health authorities in order to receive treatment. The availability of a simple, rapid and inexpensive test would aid in recognition and control of this disease.

The usual clinical evidence of a gonorrheal infection in the male is a purulent discharge from the meatus and urethra of the penis. As routine procedure it is necessary to make a differential diagnosis of the nature of the discharge before antibiotics can be prescribed. As a rule the first test is to determine if the urethritis is gonococcal or non-specific in nature. An object of this invention is therefore to provide a system which will operate directly from the patient and give the clinician or physician a differential diagnostic tool which is time saving, inexpensive and reliable.

As a screening test for gonorrhea in public V-D clinics, hospitals, physicians' offices and the Armed Forces, the present device would serve as an inexpensive and accurate differential diagnostic aid to assist the physician or clinic in the choice of drug treatment. The need for a simple and inexpensive diagnostic system that can function in the field, independent of bacteriological and microscopic tests, is therefore well established. One of the difficulties in making a quick and reliable diagnosis of male infection is the initial confusing similarity with urethritis.

A urethral exudate in the male may appear as a result of the following other causes: prostatitis, trauma, *Escherichia coli*, staphylococcus, tuberculosis, balanitis, ingested urethral irritants, cantharides, vegetables rich in oxalates, and others may precipitate urethral inflammation. Pellagra, diabetes and gout are responsible in some cases, *Trichomonas vaginalis* can be found in fair frequency in abacterial urethritis. *Entomoeba histolytica* as a cause of urethral discharge is found exclusively in the presence of recto-urethral or vesical fistula. Bilfarizia is a metozoan that produced urethritis rather frequently in endemic areas. Such systemic diseases as typhoid, mumps, influenza and smallpox can, if septicemic, produce urethritis.

In a large percentage of individuals with acute or chronic urethral discharge, although suspected of having a gonorrheal infection, demonstration of the Neisseria is not possible. Many of these are treated as gonococcal infections and it is only when they persist, subsequent to a variety of therapeutic measures, that their abacterial nature may be recognized. Subsequent thorough examinations of the entire anterior and posterior urethra and upper urinary tract may reveal that the signs of inflammation are present but that structural deformity is not predispositional, and, further, that etiologic organisms are totally absent.

It has been estimated that 80 per cent of nonspecific urethritides are abacterial. Two forms are prevalent: the acute type, resembling acute gonorrhea, and the subacute or Welsch type. Abacterial pyuric conditions of the prostate and upper urinary tract have been known to exist a long time, and occasionally the urethritis is associated with symptons referable to the upper urinary tract. The acute abacterial urethritis usually has its inception one to five days after intercourse. A profuse purulent discharge occurs with reddening of the meatus and accompanying dysuria. Posterior urethral involvement may be indicated by frequency, urgency, and terminal hematuria. The clinical picture is so similar to that seen in gonorrhea that it is confusing when the Neisseria is not demonstrable.

The differential diagnosis of a urethral discharge rests upon exclusion of the urethritides appearing in gonorrhea as the first step, secondary to other bacteria, foreign body, trauma, local neoplastic and specific inflammatory diseases, sensitivity reactions, urethral manifestations of systemic disease and infestation with protoxoa, metazoa and fungi.

The principal object of this invention is to provide a diagnostic system which will detect *Neisseria gonorrhoeae* in the male without culture or the classical gram-staining method, both of which are time consuming and expensive to perform and require trained technicians and laboratory equipment.

The present invention involves the use of a reagent from the group of oxidase testing reagents known as phenylenediamines, including the following: p-Amino Dimethylaniline Oxalate, N. N-Dimethyl-p-Phenylenediamine Dihydrochloride, N, N-Dimethyl-p-Phenylenediame Oxalate, N, N-Dimethyl-p-Phenylenediamine Monohydrochloride and N, N, N' N' Tetra-Methyl-p-Phenylenediamine Dihydrochloride. A pledget or carrier of any suitable material such as dacron fiber, cotton fiber or other porous material is impregnated or saturated with one of these reagents under certain conditions hereinafter disclosed and then dried. It remains in the dry state until it is activated by a wetting agent.

The pledget is the principal component of the diagnostic system, as it contains the reactive chemical that is capable of identifying the gonococcus. In the dry state the pledget as prepared by this method will remain stable and is capable of long shelf life. The second part of the system is the wetting agent which is separated from the pledget by virtue of being contained in a frangible ampul. When the frangible ampul is crushed the wetting agent contained therein is released, activating the reagent in the pledget. The pledget after being highly sensitized is brought into contact with the specimen on the tip of the collecting swab, reacting with the gonococci present, causing the specimen located on the swab to take on a charactaristic color depending on the choice of reagent used. The pledget being nearly colorless in appearance does not cause a confusing reaction because it does not react colorimetrically. The color change takes place on the specimen collected on the swab. The reaction time to indicate a positive specimen usually falls within the range of from 30 to 120 seconds.

The wetting agent contained in the ampul may consist of water, physiological saline, pH buffer solutions, or any other solutions or combinations of solutions which enhance or sensitize the oxidase reaction. The control of pH of the wetting agent is desirable to prevent autooxidation of the reagent in the pledget. The preferred pH range of the wetting agent should be 6.5 to 7.2.

In order to illustrate more fully the manner in which the test is made using the foregoing reagents, reference is made to the drawing, wherein:

FIG. 1 is an elevational view of one type of instrument suitable for use in practicing my method for detecting *Neisseria gonorrhoeae*, showing the instrument prior to use in a test in the form sold as a packaged system consisting of two basic parts; and FIG. 2 is an elevational view of the instrument shown in FIG. 1 after it has been used in making a test.

Referring more specifically to the drawing, which represents one type of instrument capable of performing my test procedure, numeral 10 indicates a tube of transparent, flexible plastic, into which is inserted a pledget 12 of cotton impregnated or saturated with the reagent and dried. The pledget is seated on a frangible glass ampul 14 disposed in the closed end of the tube and a cap 16 is placed over the open end of the tube, sterile swab 18 with a plastic handle 20 to be used in obtaining a specimen of exudate is sealed in a separate sterile envelope 22, and the tube and envelope are packaged together in an envelope or other suitable container (not shown). While the wall structure of the plastic tube is flexible, it has sufficient rigidity normally to maintain a generally cylindrical shape and to permit easy insertion of the swab after a specimen of exudate has been taken. The ampul contains a suitable wetting agent, as described herein, and is sufficiently frangible that it can readily be broken when the sides of the flexible tube are pressed inwardly between the thumb and forefinger, whereupon the ampul shatters and permits its fluid contents to wet the material impregnated in the pledget, which normally is pushed into the fluid and fragmented glass when the swab is inserted in the tube. When the swab containing the specimen contacts the pledget, reaction between the specimen on the swab and the reagent in the pledget commences immediately and, if gonococci are present, the specimen on the swab changes color, normally to purple, red-orange, or dark gray, depending upon the reagent used in the pledget, thus indicating a positive test. The reaction time to indicate a positive specimen usually falls within the range of from 30 to 120 seconds.

A preferred method selected from the above for the manufacture of the pledget and the preparation of a wetting agent is illustrated as follows:

A 1% solution of N, N, N' N' Tetra Methyl-p-Phenylenediamine Di-hydrochloride is prepared as follows: 1 gram of the reagent is added to 35 ml distilled water that has been brought to a boil and allowed to cool to room temperature. Solution is effected by rapid stirring. 64 ml of Ethyl Alcohol (Fisher A-407) is then added and stirred. Strips of cotton Webril, $\mu$ inch wide 20 inches long, are then dipped one at a time into the solution, placed on nylon screen in a horizontal position and allowed to air-dry. The dry strips are then cut into pieces 9/16 inch long. These become the pledgets.

A physiological saline solution is prepared by adding 0.85 grams of Sodium Chloride to 99 ml distilled water and the pH adjusted to 7.0. This solution becomes the wetting agent. Frangible ampuls containing ½ ml of this solution are prepared, as this is the quantity necessary to adequately wet the ¾ inch × 9/16 " pledget.

The ampul, approximately 7 mm in diameter and 35 mm in length, is placed at the bottom of a flexible plastic tube approximately 8 mm inside diameter and 160 mm long. A pledget manufactured by the above technique is rolled up and pushed down the tube so that it is in contact with the ampul. A telescopic cap approximately 65 mm in length is positioned over the open end of the plastic tube, capping the system.

A sterile dacron swab, mounted on a plastic stick approximately 150 mm long is packaged together with the reagent system and this combination becomes the diagnostic instrument. This swab is separately contained in its own sterile glassine envelope.

The above two units comprising a single package are adapted to be sold through normal pharmaceutical channels to physicians, clinics, and hospitals and the package is immediately available for a test and prompt diagnoses of the patient's condition at the site of specimen collection. When a diagnostic test for gonorrhea is to be made, the package is opened and the sterile swab is removed from its envelope, and a specimen of exudate collected to the tip of the swab. The telescopic cap is then removed from the plastic tube and the swab is inserted, tip first, into the plastic tube. The telescopic cap is then replaced. The flexible tube is then squeezed at the ampul portion, breaking same and releasing its contents. Simultaneously, the telescopic cap is pushed down, forcing the specimen containing swab into contact with the pledget. This action also forces the pledget down into the wetting agent, activating the system. The specimen on the swab turning purple within two minutes in a positive test for gonorrhea. The swab may be withdrawn from the pledget by about one inch to facilitate reading of the test results, i.e., the foregoing change in color of the specimen on the swab. The use of this test, therefore, gives the physician or clinician a rapid and accurate diagnostic tool in the first step of his differential diagnosis.

To illustrate further the sensitivity of this system and its ability to detect the gonococcus precisely at the point of specimen collection on the swab, the above procedure is repeated and a culture of *Neisseria gonorrhoeae* is used as being representative of the exudate in the foregoing example. In this example the swab is used to pick a few colonies from a petri dish culture. The identical procedure is used with the instrument. A distinct purple coloration of the bacteria on the swab will be observed within one minute. The nearly colorless pledget and the white background of the dacron swab make the identification of the organisms on the swab clear and distinct, just as it is with the exudate directly from a patient.

While some prior are, U.S. Pat. No. 3,450,129, Avery et al, makes use of frangible ampuls for carrying reagents, the use of that method is directed specifically to transporting a specimen to a laboratory and using their method for the purpose of preserving the viability of the bacteria until they can be cultured, whereas this is a diagnostic system and does not require culture. It is a direct test. Diagnosis is made at the time of collection of the specimen.

While only a few examples of my diagnostic reagent system and reagents have been described in detail herein, various changes and modifications may be made without departing from the scope of the invention.

I claim:

1. A swabbing instrument for use in the rapid detection of *Neisseria gonorrhoeae* without gram-staining and without culture by providing an initial distinctive color change on the swab of the instrument after collecting an inoculum on the swab, said instrument consisting essentially of:

a stick for the swab used to collect the inoculum;

a sterile swab mounted on said stick for obtaining a clinical specimen of said Neisseria from the penis as an exudate and the only inoculum of bacteria at the collection site from the patient;

a tube of transparent plastic having flexible side walls and a closed end into which the swab and inoculum are inserted by the stick;

a dry substantially colorless pledget disposed in said tube which is impregnated with a dilute colorless solution of N, N, N' N' tetramethyl-p-phenylenediamine dihydrochloride in alcohol which has been dried;

a frangible ampul containing a wetting activating agent for said tetramethyl-p-phenylenediamine compound in said tube;

said dry pledget placed above said ampul and reacting when wetted after breaking of said ampul to wet said swab without coloration but to react with *Neisseria gonorrhoeae* in the inoculum on said swab to produce a distinctive initial color change;

said wetting activating agent constituting the sole liquid agent to activate said dry pledget and said agent being selected from the group consisting of water, physiological saline, and aqueous buffer solutions at pH 6.5 to 7.2; and, said initial distinctive color change being a purple shade produced on the inoculum on said swab at the site of collection of the bacteria, after said clinical specimen of exudate is taken from the patient and the swab is placed on the wetted pledget, wetted with said activating agent, and within two minutes to be directly indicative of *Neisseria gonorrhoeae* bacteria in said specimen.

2. An instrument as claimed in claim 1 wherein said sterile swab is packaged in a sealed envelope.

3. A swabbing instrument for use in the rapid detection of *Neisseria gonorrhoeae* without gram-staining and without culture by providing an initial distinctive color change on the swab of the instrument after collecting an inoculum on the swab, said instrument consisting essentially of;

a stick for the swab used to collect the inoculum;

a sterile swab mounted on said stick for obtaining a clinical specimen of said Neisseria from the penis as an exudate and the only inoculum of bacteria at the collection site from the patient;

a tube of transparent plastic having flexible side walls and a closed end into which the swab and inoculum are inserted by the stick;

a dry substantially colorless pledget disposed in said tube which is impregnated with a dilute colorless solution in alcohol of a phenylenediamine agent selected from the group consisting of p-amino dimethylaniline oxalate, N, N-dimethyl-p-phenylenediamine dichloride, N, N-dimethyl-p-phenylene-diamine oxalate, N, N-dimethyl-p-phenylenediamine monohydrochloride and N, N, N' N' tetramethyl-p-phenylenediamine dihydorchlide which has been dried:

a frangible ampul containing a wetting activating agent for said phenylenediamine agent in said tube;

said dry pledget placed above said ampul and reacting when wetted after breaking of said ampul to wet said swab without coloration but to react with *Neisseria gonorrhoeae* in the inoculum on said swab to produce a distinctive initial color change;

said wetting activating agent constituting the sole liquid agent to activate said dry pledget and said agent being selected from the group consisting of water, physiological saline, and aqueous buffer solutions at pH 6.5 to 7.2; and, said initial distinctive color change being a purple shade produced on the inoculum on said swab at the site of collection of the bacteria, after said clinic specimen of exudate is taken from the patient and the swab is placed on the wetted pledget, wetted with said activating agent, and within two minutes to be directly indicative of *Neisseria gonorrhoeae bacteria* in said specimen.

4. An instrument as claimed in claim 3 wherein said sterile swab is packaged in a sealed envelope.

* * * * *